US012746323B2

(12) United States Patent
Yaroslavsky et al.

(10) Patent No.: US 12,746,323 B2
(45) Date of Patent: Sep. 29, 2026

(54) SMART IRRIGATION AND ASPIRATION SYSTEM AND METHOD

(71) Applicant: IPG PHOTONICS CORPORATION, Marlborough, MA (US)

(72) Inventors: Ilya Yaroslavsky, Oxford, MA (US); Sergei Pilipetskii, Oxford, MA (US); Dmitri Boutoussov, Oxford, MA (US); Gregory Altshuler, Oxford, MA (US); Olivier Traxer, Oxford, MA (US); Isaac Ostrovsky, Oxford, MA (US); Anastasiya Kovalenko, Oxford, MA (US); Felix Stukalin, Oxford, MA (US)

(73) Assignee: IPG PHOTONICS CORPORATION, Marlborough, MA (US)

( * ) Notice: Subject to any disclaimer, the term of this patent is extended or adjusted under 35 U.S.C. 154(b) by 405 days.

(21) Appl. No.: 18/289,289

(22) PCT Filed: May 4, 2022

(86) PCT No.: PCT/US2022/027625
§ 371 (c)(1),
(2) Date: Nov. 2, 2023

(87) PCT Pub. No.: WO2022/235762
PCT Pub. Date: Nov. 10, 2022

(65) Prior Publication Data

US 2024/0238501 A1 Jul. 18, 2024

Related U.S. Application Data

(60) Provisional application No. 63/183,675, filed on May 4, 2021.

(51) Int. Cl.
*A61M 1/00* (2006.01)

(52) U.S. Cl.
CPC ....... *A61M 1/77* (2021.05); *A61M 2205/3334* (2013.01); *A61M 2205/3344* (2013.01); *A61M 2210/1082* (2013.01)

(58) Field of Classification Search
CPC ... A61B 18/26; A61B 2217/005; A61B 1/307; A61M 1/77; A61M 2205/3344; A61M 1/732
See application file for complete search history.

(56) References Cited

U.S. PATENT DOCUMENTS 5,685,840 A 11/1997 Schechter et al.
2008/0082077 A1 4/2008 Williams
(Continued)

FOREIGN PATENT DOCUMENTS

WO 2020140072 A1 7/2020

*Primary Examiner* — William R Carpenter
(74) *Attorney, Agent, or Firm* — Caroline J. Roush, Esq.

(57) ABSTRACT

An irrigation and aspiration system that includes a catheter shaft having a distal end that is in fluid communication with an interior of a kidney, an irrigation channel and an aspiration channel extending through the shaft, a bypass channel fluidly coupled with the irrigation channel and the aspiration channel a bypass valve configured to control a level of fluid communication between the irrigation and aspiration channels via the bypass channel, an aspiration pump, at least one valve disposed on the aspiration channel and configured to provide a pulsed flow of fluid in the aspiration channel, a pressure sensor in fluid communication with an interior of the kidney, and a controller configured to: receive at least one pressure measurement, compare the measured pressure to a threshold, and based on the comparison, send a control command to at least one of the bypass valve, aspiration pump, and the at least one valve.

12 Claims, 8 Drawing Sheets

(56) References Cited

U.S. PATENT DOCUMENTS

| | | | |
|---|---|---|---|
| 2008/0125697 | A1 | 5/2008 | Gao |
| 2008/0249483 | A1 | 10/2008 | Slenker et al. |
| 2019/0247566 | A1 | 8/2019 | Hassidov et al. |
| 2020/0187761 | A1 | 6/2020 | Shelton |
| 2020/0206472 | A1* | 7/2020 | Ma .......................... A61M 1/85 |
| 2020/0397974 | A1 | 12/2020 | Germain et al. |
| 2021/0085158 | A1* | 3/2021 | Ikuma ................ A61B 1/00068 |
| 2021/0121188 | A1 | 4/2021 | Yurek |

* cited by examiner

SMART IRRIGATION AND ASPIRATION SYSTEM AND METHOD

PRIORITY

This application claims the benefit of priority under 35 U.S.C. § 119 to U.S. Provisional Patent Application Ser. No. 63/183,675, titled SMART IRRIGATION AND ASPIRATION SYSTEM, filed on May 4, 2021, which is incorporated by reference herein in its entirety and for all purposes.

BACKGROUND

Technical Field

The technical field relates generally to laser lithotripsy, and more specifically to laser-assisted removal of kidney stones using a ureteroscope with an emphasis on pressure control within the kidney.

Background Discussion

Kidney stone disease is a prevalent condition estimated to be affecting 12% of the world population. Although most of the patients can pass the stones naturally, the condition can be severe enough such that medical intervention is required. Extreme pain, nausea, vomiting, infection, blockage of urine flow, and loss of kidney function can follow. Laser lithotripsy is a method for treating kidney stones. Light energy directed by an optical fiber is used to break the stone into finer parts that can be passed naturally. Conventional approaches to kidney stone treatment with flexible ureteroscopes include devices with forced fluidic irrigation and natural aspiration through space between the shaft of the ureteroscope and access sheath or natural urinal tract. More recent approaches include devices that are also configured with an aspiration channel within the ureteroscope to vacuum stone fragments and dust that result from stone ablation (see, for example, U.S. Patent Publication No. 2017/0215965).

One of the problems of laser lithotripsy is stone targeting. When the optical fiber is not in contact with the stone, ablation rates will be low, which increases the procedure time. Furthermore, the laser pulse might be misdirected toward unintended targets, causing collateral damage. Another problem is the maintenance of pressure and fluid equilibrium in the kidney and ureteroscope during the procedure. Applying a vacuum to remove stone fragments changes the fluid content and pressure within the kidney, and if not properly managed, has the potential to cause unintended damage to the patient or to the ureteroscope. Furthermore, during laser lithotripsy procedures a vacuum is created in the aspiration channel of the ureteroscope. The distal end of this channel can often get clogged by stones and their fragments. Severe clogging may necessitate repeated removal, cleaning, and reinsertion of the ureteroscope during an operation.

SUMMARY

Aspects and embodiments are directed to a method and system for controlling fluid flow in an irrigation and aspiration system.

In accordance with an exemplary embodiment, there is provided an irrigation and aspiration system that includes a catheter shaft having a proximal end and a distal end, the distal end in fluid communication with an interior of a kidney, an irrigation channel extending through the shaft from the proximal end to the distal end, an aspiration channel extending through the shaft from the proximal end to the distal end, a bypass channel fluidly coupled with the irrigation channel and with the aspiration channel, a bypass valve configured to control a level of fluid communication between the irrigation channel and the aspiration channel via the bypass channel, an aspiration pump in fluid communication with the aspiration channel and configured to pump fluid from a distal end toward a proximal end of the aspiration channel, at least one valve disposed on the aspiration channel and configured to provide a pulsed flow of fluid in the aspiration channel, a pressure sensor in fluid communication with an interior of the kidney, and a controller in communication with the pressure sensor, the bypass valve, the at least one valve, and the aspiration pump, the controller configured to: receive at least one pressure measurement value from the pressure sensor, compare the measured pressure value to a predetermined pressure threshold, and based on the comparison, send a control command to at least one of the bypass valve, the at least one valve, and the aspiration pump.

In one example, the controller is configured to calculate a measured pressure value per unit of time and determine whether the measured pressure value per unit of time meets or exceeds a first predetermined threshold value, and in response send a control command to the aspiration pump such that a flow rate of fluid in the aspiration channel is increased. In one example, the measured pressure value used as a basis for the first predetermined threshold value is 50 $cmH_2O$.

In one example, the controller is configured to determine whether the measured pressure value per unit of time meets or exceeds a second predetermined threshold value, and in response send a control command to the bypass valve such that the bypass channel is opened and the irrigation channel is fluidly coupled to the aspiration channel and irrigation fluid is directed toward the distal end of the aspiration channel. In one example, the measured pressure value used as a basis for the second predetermined threshold value is 60 $cmH_2O$.

In one example, the controller is configured to implement the pulsed flow of the fluid by sending a control command to close the at least one valve for a predetermined time duration $\tau 1$ and close the at least one valve for a predetermined time duration $\tau 2$ in repetitive cycles, where $\tau 1$ and $\tau 2$ are separated by a predetermined time period t and each cycle is of a time period T. In one example, the at least one valve is disposed on the aspiration channel between the bypass channel and the aspiration pump.

In one example, the at least one valve includes a first valve and a second valve, the second valve disposed on the aspiration channel between the bypass channel and the distal end of the aspiration channel. In a further example, the controller is configured to implement the pulsed flow of the fluid by sending a control command to close the first valve for a predetermined time duration $\tau 1$ and close the second valve for a predetermined time duration $\tau 2$ in repetitive cycles, where $\tau 1$ and $\tau 2$ are separated by a predetermined time period t and each cycle is of a time period T.

In one example, the bypass valve is configured as a three-way solenoid pinch valve and the at least one valve is configured as a two-way solenoid pinch valve.

In one example, the pressure sensor is in proximity to an external surface of the catheter shaft.

In one example, the system further includes a laser source configured to emit laser radiation, and an optical fiber coupled to the laser source and configured to transmit the laser radiation within close proximity to the distal end of the aspiration channel, the optical fiber extending from the proximal end to the distal end of the catheter shaft.

In accordance with another exemplary embodiment, there is provided a method of operating an aspiration and irrigation system that includes providing pulsed fluid flow from a distal end to a proximal end of an aspiration channel, the distal end of the aspiration channel in fluid communication with an interior of a kidney, measuring a pressure value in the interior of the kidney, determining whether the measured pressure value is less than a first pressure threshold, and increasing a rate of the pulsed fluid flow when the measured pressure value meets or exceeds the first pressure threshold.

In one example, the method further includes providing fluid flow from a proximal end to a distal end of an irrigation channel, the distal end of the irrigation channel in fluid communication with the interior of the kidney, determining whether the measured pressure value is less than a second pressure threshold, and directing fluid flow from the irrigation channel into the aspiration channel when the measured pressure value meets or exceeds the second pressure threshold. In one example, the fluid flow from the irrigation channel into the aspiration channel is directed through a bypass channel. In another example. The method further includes closing a valve disposed on the aspiration channel between the proximal end of the aspiration channel and the bypass channel.

In one example, the pulsed fluid flow is implemented by at least one valve disposed on the aspiration channel. In one example, the pulsed fluid flow is implemented by closing the at least one valve for a predetermined time duration $\tau1$ and closing the at least one valve for a predetermined time duration $\tau2$ in repetitive cycles, where $\tau1$ and $\tau2$ are separated by a predetermined time period t and each cycle is of a time period T. In another example, the at least one valve includes a first valve and a second valve, and the pulsed fluid flow is implemented by closing the first valve for a predetermined time duration $\tau1$ and closing the second valve for a predetermined time duration $\tau2$ in repetitive cycles, where $\tau1$ and $\tau2$ are separated by a predetermined time period t and each cycle is of a time period T. In one example, $\tau1$ and $\tau2$ are within a range of 20 to 500 ms inclusive and the time period T is within a range of 0.5 to 3.0 s inclusive.

Still other aspects, embodiments, and advantages of these example aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Embodiments disclosed herein may be combined with other embodiments, and references to "an embodiment," "an example," "some embodiments." "some examples." "an alternate embodiment." "various embodiments," "one embodiment," "at least one embodiment," "this and other embodiments," "certain embodiments," or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

As discussed above, problems associated with laser lithotripsy include stone targeting, maintaining pressure and fluid equilibrium in the kidney, and clogging from stone debris. The solutions disclosed herein seek to overcome these problems and ensure safe and effective outcomes of clinical procedures by implementing systems and methods that synchronize the functions of a laser and fluidic pump system via monitoring and real time control of irrigation, aspiration, and laser radiation operating parameters.

In accordance with various aspects, smart irrigation and/or aspiration flow is implemented to increase the efficiency of aspiration and to prevent clogging. As used herein, the term "smart" in reference to irrigation and/or aspiration flow refers to the ability to maintain two-way communication (i.e., transmit or receive a signal) with a controller. During laser treatment, negative pressure in the aspiration channel in combination with irrigation fluid flow from the outlets of the irrigation channel create a flow of small stone particles and dust in the aspiration channel that are the result of the ablation process. It is critical to balance these in- and out-flows for purposes of keeping the kidney pressure in a safe range. In accordance with embodiments described herein, several functions can be implemented to keep the aspiration channel free from clogging with ablation particles and to remain open for fluid flow:

Liquid pressure monitoring in the treatment area (kidney)

Continuous pulsing of aspiration flow

Varying negative pressure in the aspiration channel as a result of pressure monitoring Switching irrigation flow into the aspiration channel to remove clogging Clog Detection and Kidney Pressure Control In accordance with various embodiments, the disclosed irrigation and aspiration system comprises one or more sensors such as flow sensors (also referred to as fluid rate or flow rate sensors) and pressure sensors, at least one valve, fluid pumps, and a processing computer functioning as a controller or as part of a control system.

Figure 1A:
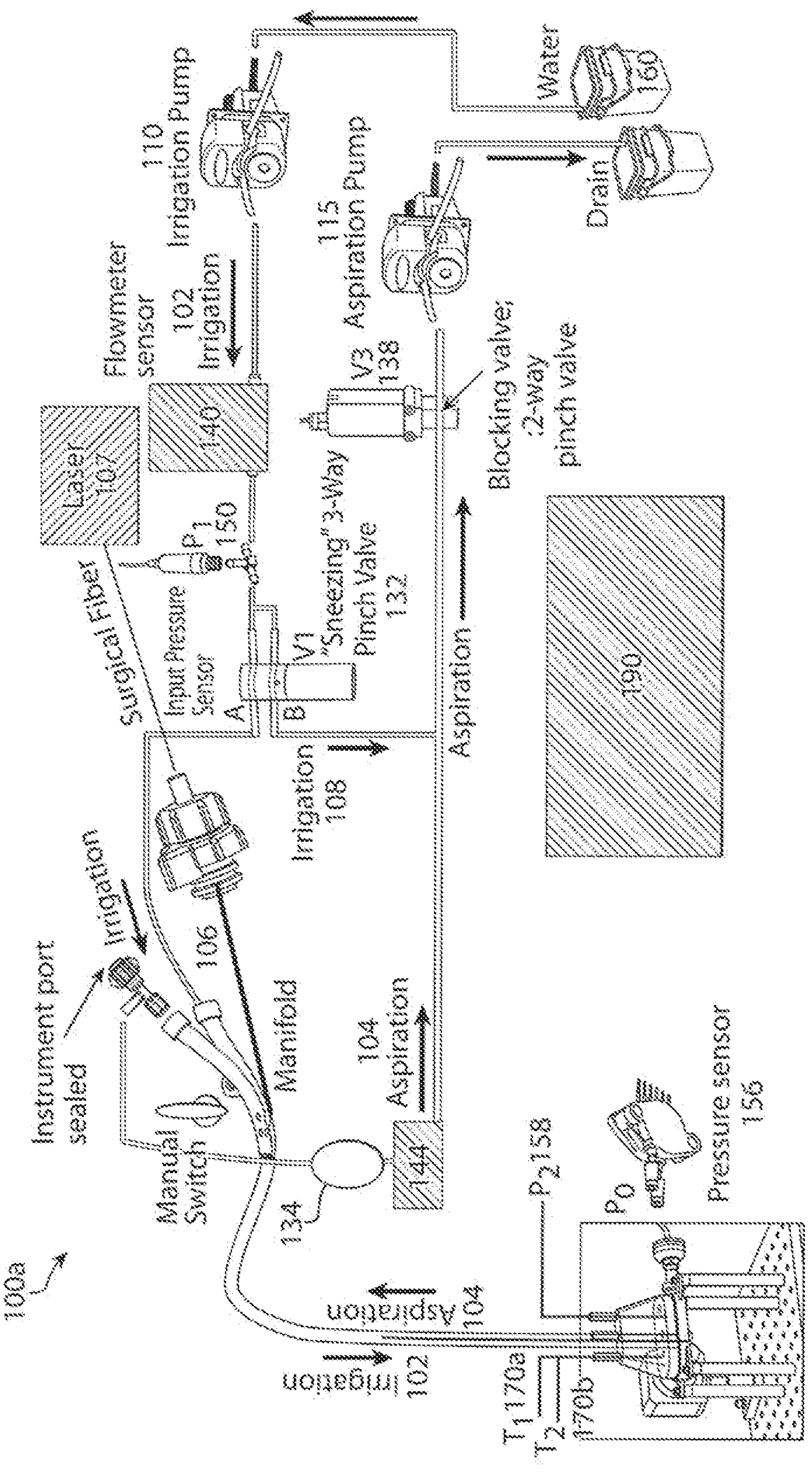
FIG. 1A is a schematic representation of one example of an irrigation and aspiration system in accordance with aspects of the invention.

One non-limiting example of an irrigation and aspiration system in accordance with one embodiment is indicated generally at 100*a* in FIG. 1A. System 100*a* comprises a catheter shaft 112 (see FIGS. 2 and 3) having a proximal end 113 and a distal end 114, where the distal end 114 is in fluid communication with an interior of a kidney, an irrigation channel 102, an aspiration channel 104, a bypass channel 108, a bypass valve 132, at least one valve disposed on the aspiration channel (e.g., valve 138), an aspiration pump 115, one or more pressure sensors 156, 158, and a controller 190.

Figure 3:
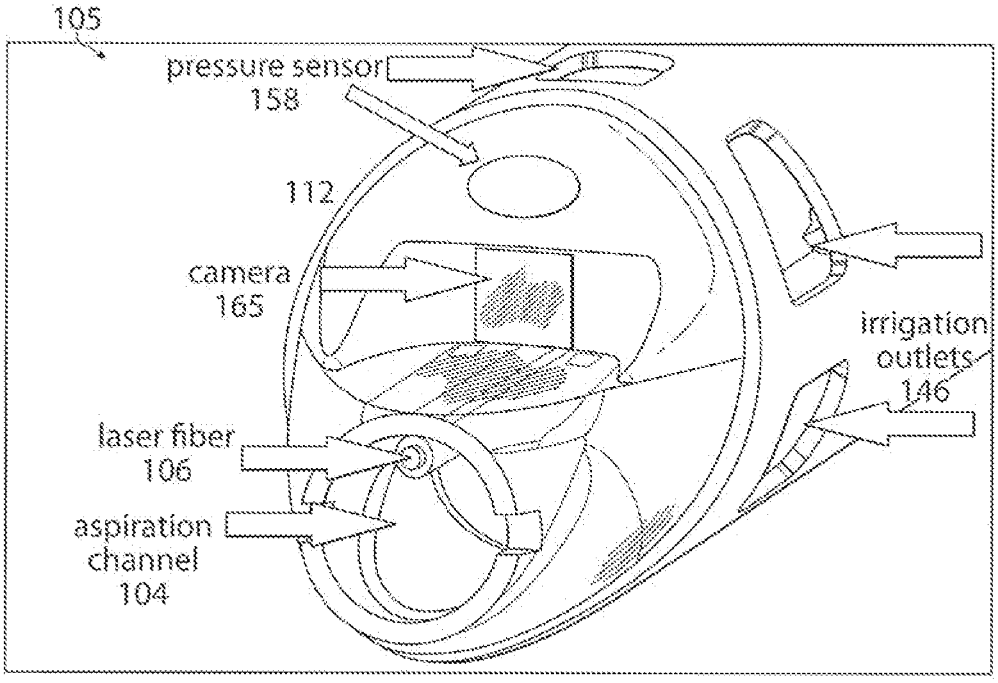
FIG. 3 is a perspective view of the distal end of one example of a ureteroscope in accordance with aspects of the invention.

The irrigation channel 102 and aspiration channel 104 extend through the shaft 112 from the proximal end 113 to the distal end 114. A distal end of both the irrigation channel 102 and the aspiration channel 104 is in fluid communication with the interior of the kidney. The aspiration/irrigation system 100*a* is used within a ureteroscope 105, also called a "three-channel" ureteroscope (for fiber, aspiration, and irrigation). Fluids are pumped in (e.g., to the kidney) through the irrigation channel 102, and pumped out of the kidney through the aspiration channel 104. The term "proximal end" when used in reference to the channel refers to the end attached at the corresponding pump, while the term "distal end" refers to the end that is exposed in the ureteroscope (for example, the distal end is indicated in FIG. 3) such that when the distal end is in position for a lithotripsy procedure, it is within an interior volume of the kidney.

The bypass channel 108 is fluidly coupled with the irrigation channel 102 and the aspiration channel 104, and the bypass valve 132 is configured to control a level of fluid communication between the irrigation channel 102 and the aspiration channel 104 via the bypass channel 108, as discussed in more detail below. The aspiration pump 115 is in fluid communication with the aspiration channel 104 and is configured to pump fluid from the distal end toward a proximal end of the aspiration channel 104. In this embodiment, the at least one valve disposed on the aspiration channel 104 includes valve 138 that is disposed between the bypass channel 108 and the aspiration pump 115.

Pressure sensors 156 and 158 are in fluid communication with an interior of the kidney, and are each configured to measure pressure. In some embodiments, the catheter 112 is configured with a pressure sensor 158, FIG. 3 shows two possible locations for pressure sensor 158, each of which is positioned at or near the distal end 114 of the catheter shaft 112. In some embodiments, as shown in FIG. 3, pressure sensor 158 may be in proximity to an external surface of the catheter shaft 112. For instance, the external surface of catheter shaft 112 in the example shown in FIG. 3 has a small recess that houses pressure sensor 158. According to another example, and as shown in FIG. 3, pressure sensor 158 is positioned in proximity to a camera 165 of the ureteroscope 105, e.g., on a surface above the camera 165.

In some embodiments, the pressure sensor 156 is disposed through a separate insertion device into the kidney. In this instance, the pressure sensor 156 is disposed external to the catheter shaft 112 (and not attached or otherwise integrated with the catheter shaft 112), and is also referred to herein as an "external" pressure sensor. For example, a miniature pressure sensor may be inserted into the kidney via a needle and/or catheter, or any other access sheath and is therefore external to the ureteroscope (i.e., external to the catheter shaft, aspiration channel, and irrigation channel). According to some embodiments, pressure sensor 156 has at least one dimension (e.g., diameter or length) that is less than 19 millimeters (mm), in further embodiments has at least one dimension that is less than 15 mm, and in yet further embodiments has at least one dimension that is less than 11 mm. In accordance with certain embodiments, the pressure sensor 156 has a diameter less than 0.5 mm, and in one embodiment has a diameter less than 0.3 mm. In certain embodiments, the pressure sensor 156 has a length less than 6 mm, and in one embodiment has a length less than 5 mm. Pressure sensor 156 may be positioned within the kidney such that it is in proximity to the distal end of the catheter shaft 112 and provides in-vivo monitoring of the pressure within the kidney.

In accordance with one or more embodiments, the at least one valve disposed on the aspiration channel 104 is configured to provide a pulsed flow of fluid in the aspiration channel 104. In system 100*a* of FIG. 1, valve 138 is configured to provide the pulsed flow of fluid in the aspiration channel 104. Valve 138 is configured as a pinch valve, such as a two-way solenoid pinch valve. When these types of valves are not energized, a plunger opens, which allows fluid to flow through the valve via inlet and outlet ports. When the plunger is energized, the plunger closes, compressing the aspiration tubing and completely cutting off fluid flow. At the same time, as a result of the compression of the aspiration tubing, a small amount of liquid is pushed back along the aspiration line. In some embodiments, the controller 190 is configured to implement the pulsed flow of fluid in the aspiration channel by sending one or more control commands to at least one of the aspiration pump 115 and valve 138. Controller 190 is configured to send a control command to valve 138 to open or close. The aspiration pump 115 may also be controlled by controller 190 to pump fluid from the distal end to the proximal end of the aspiration channel 104, thereby "pulling" the fluid through valve 138. Valve 138 interrupts the aspiration fluid flow by sending short pulses of back-pressure along the liquid within the aspiration channel, which facilitates mixing of the particles and reduces the risk of clogging. Furthermore, the aspiration channel is constructed from materials that provide minimal stretching characteristics, i.e., a high elastic memory. According to one embodiment, the aspiration channel is constructed from a thermoplastic elastomer, such as PEBAX®.

Figure 4A:
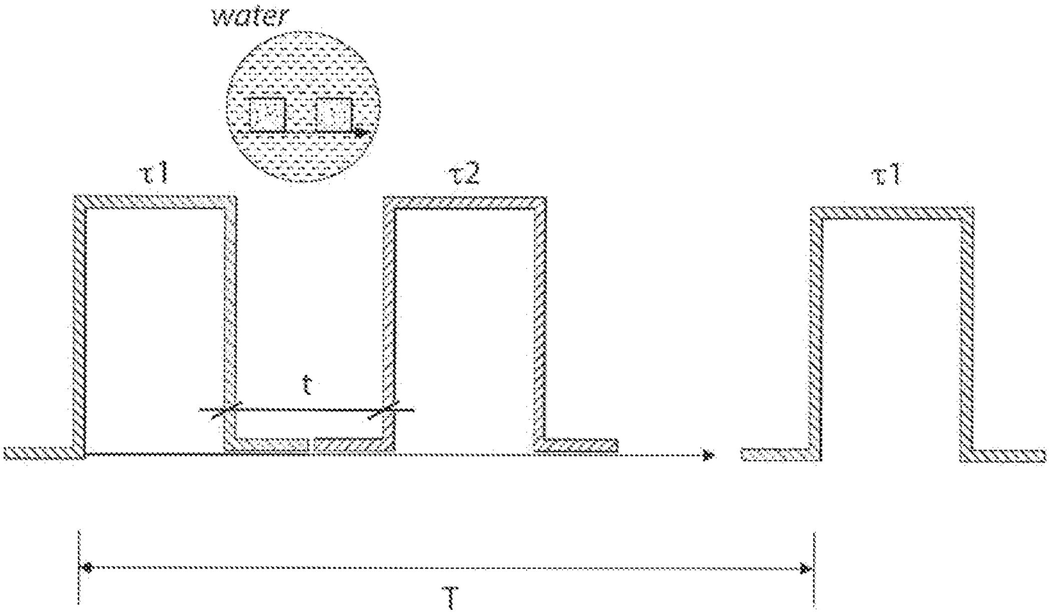
FIG. 4A is a schematic representation of one example of pulsed flow in accordance with aspects of the invention.

A schematic representation of one non-limiting example of pulsed fluid flow is shown in FIG. 4A. The controller 190 sends a control command to close valve 138 for a predetermined time duration $\tau 1$ and close valve 138 for a predetermined time duration $\tau 2$, where $\tau 1$ and $\tau 2$ are separated by a predetermined time period t in repetitive cycles, and where each cycle is of a time period T. Time period T is the time duration between the start of $\tau 1$ to the start of a consecutive $\tau 1$. The resulting pulsed flow within the fluid is also shown in FIG. 4A. In this example as shown in FIG. 4A, $\tau 1$ and $\tau 2$ are equal to each other, but it is to be appreciated that in some embodiments $\tau 1$ and $\tau 2$ are different from one another.

Figure 1B:
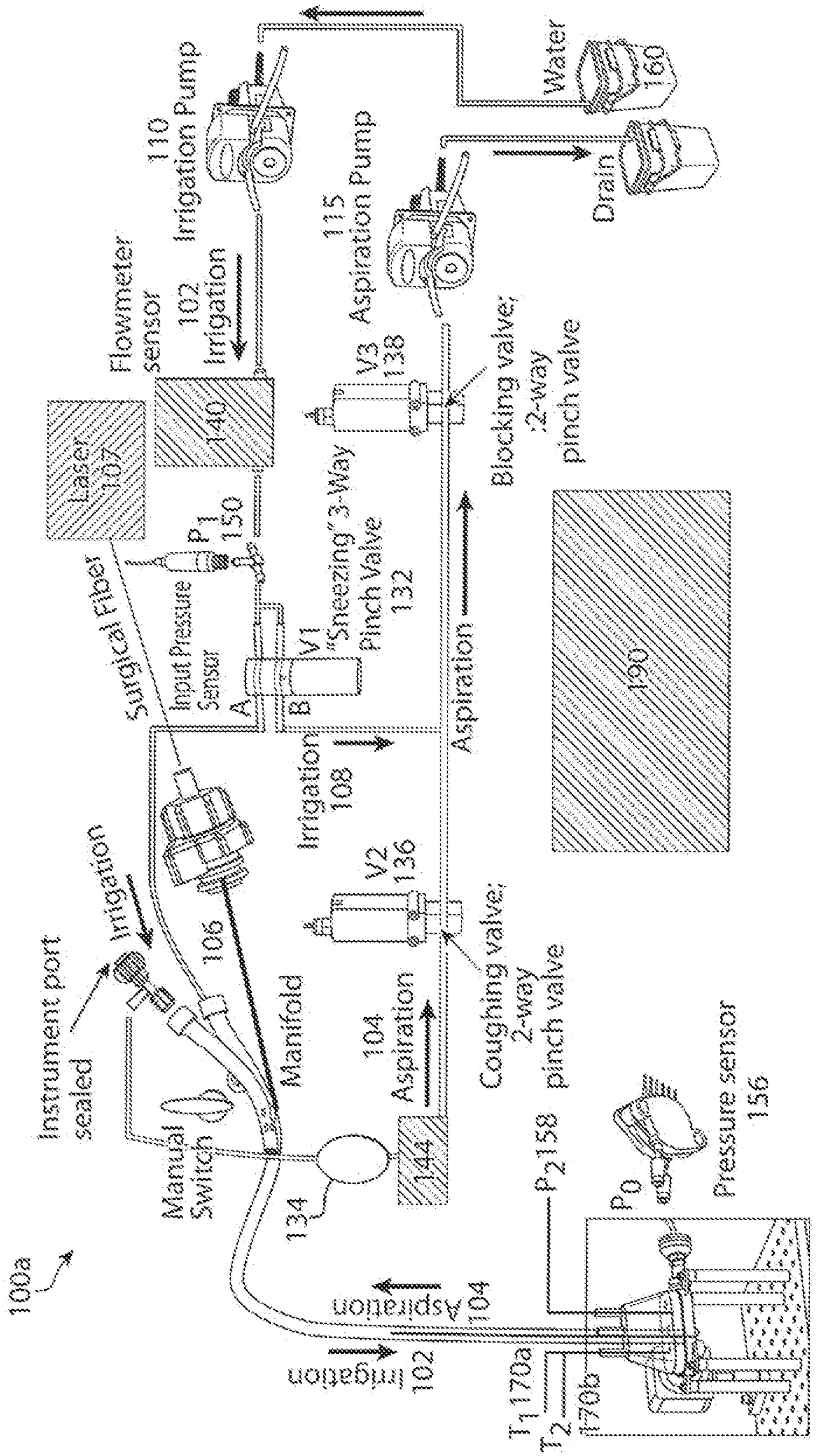
FIG. 1B is a schematic representation of another example of an irrigation and aspiration system in accordance with aspects of the invention.
Figure 4B:
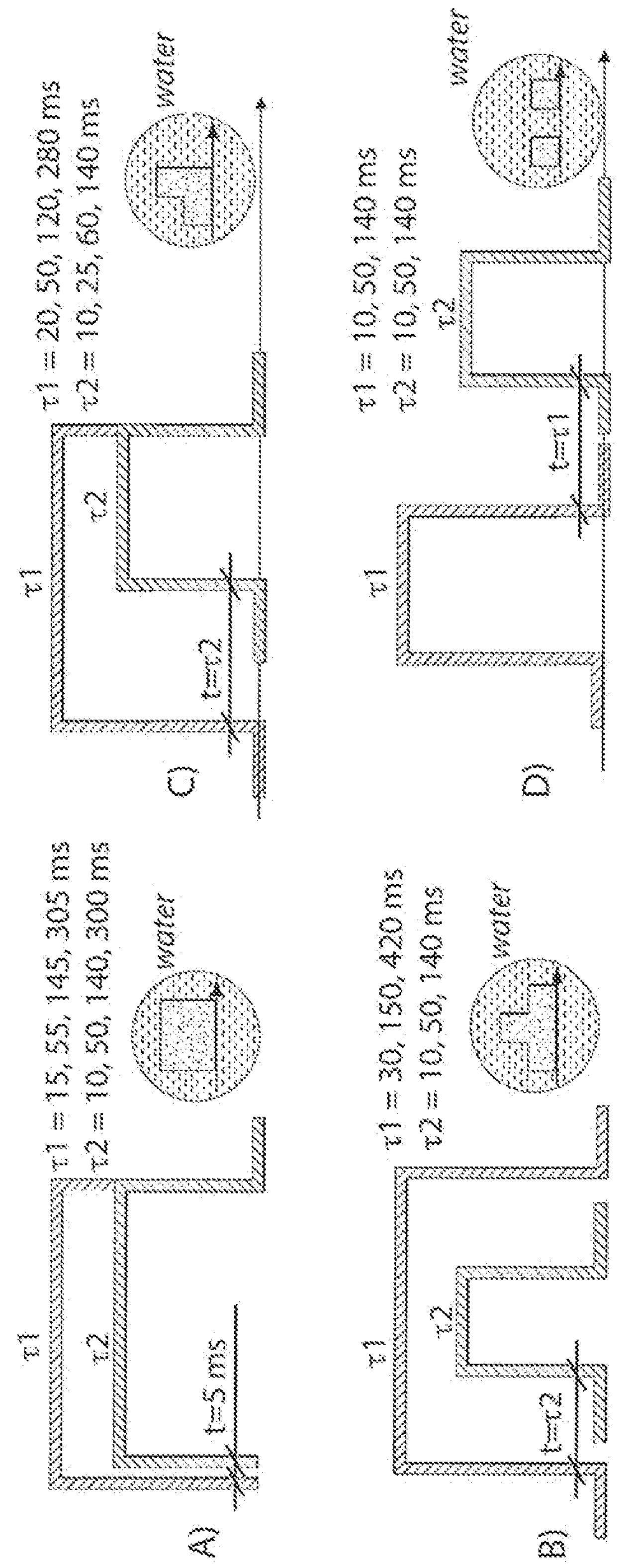
FIG. 4B is a schematic representation of other examples of pulsed flow in accordance with aspects of the invention.

Another non-limiting example of an irrigation and aspiration system in accordance with another embodiment is indicated generally at 100*b* in FIG. 1B. System 100*b* is nearly identical to system 100*a* of FIG. 1A, but in this instance, pulsed fluid flow in the aspiration channel 104 is implemented using two valves. Thus, the at least one valve of the aspiration channel 104 includes a first valve 138 and a second valve 136, where the second valve 136 is disposed on the aspiration channel 104 between the bypass channel 108 and the distal end of the aspiration channel 104. A schematic representation of one non-limiting example of the pulsed fluid flow is shown in FIG. 4A, and other examples are shown in FIG. 4B. In reference to FIGS. 4A and 4B, in this configuration controller 190 sends a control command to close the first valve 138 for a predetermined time duration τ1 and close the second valve 136 for a predetermined time duration τ2, where τ1 and τ2 are separated by a predetermined time period t in repetitive cycles, and where each cycle is of a time period 1'. As mentioned previously, time period T is the time duration between the start of τ1 to the start of a consecutive τ1. In FIG. 4A, τ1 is equal to (i.e., the same as) τ2, which is also the configuration shown in example D of FIG. 4B. In addition, the separation between τ1 and τ2 (i.e., predetermined time period t) is the time duration between the end of τ1 and the start of τ2 but in other embodiments, the predetermined time period t may be defined as the time duration between the start of τ1 and the start of τ2, as described below in reference to examples A-C of FIG. 4B.

According to other embodiments, τ1 and τ2 are not equal to each other, as shown in A, B, and C of FIG. 4B. As mentioned above, in these examples, the predetermined time period t that signifies the separation between τ1 and τ2 is defined as the time duration between the start of τ1 and the start of τ2. The combined effect of the pulses in the fluid (water) is shown in all examples of FIGS. 4A and 4B.

In some embodiments, τ1 and τ2 are each of a time duration that is within a range of to 500 milliseconds (ms) inclusive. According to some embodiments, τ1 and τ2 may have different time durations from one cycle or time period to the next. In certain embodiments, the predetermined time period t is within a range of 1 to 500 ms inclusive. In some embodiments, the predetermined time period t is within a range of 1 to 200 ms inclusive. In accordance with some embodiments, time period T is within a range of 0.5 to 3.0 seconds (s) inclusive.

Pulsed flow as implemented using at least one valve in the aspiration channel 104 provides several advantages. For one thing, pulsed flow may prevent clogging in the aspiration channel 104. In addition, pulsing the aspiration fluid flow can further enhance or otherwise increase laser ablation rates. For example, when pressure in the aspiration channel 104 is maintained at a constant or near-constant value, a situation may develop where the laser ablation crater will be growing, but the efficiency of the ablation drops because the distance from the tip of the optical fiber to the surface of the stone (i.e., bottom of the crater) continues to increase. Eventually, this may lead to a stalemate situation where the laser keeps firing, but no further stone destruction takes place. The pulsed aspiration fluid flow allows the stone to move slightly away from the aspiration channel 104 and to change position, which enables the laser to fire (the laser radiation may be implemented by a series of laser pulses) into a different location on the stone. In addition, the stone gets pulled toward the mouth of the aspiration channel 104 by the pressure pulse created by this pulsed fluid flow.

As illustrated in FIGS. 1A and 1B, systems 100*a* and 100*b* may also include a flow rate sensor 140 configured to measure a flow rate within the irrigation channel 102, a pressure sensor 150 configured to measure pressure within the irrigation channel 102, and an irrigation pump 110 in fluid communication with a source of irrigation fluid 160. Systems 100*a* and 100*b* also include a laser source 107 that provides the laser energy for the optical fiber 106. Laser energy emitted from a distal end of the optical fiber 106 functions to ablate kidney stone material.

According to at least one embodiment, a flow of irrigation fluid is initiated in system 100 by having the controller 190 send a control signal or control command to irrigation pump 110 which is configured to pump irrigation fluid from irrigation source 160 to the distal end of the irrigation channel 102. A fluid flow rate of irrigation fluid in the irrigation channel 102 can be measured by flow rate sensor 140 and the flow rate of the irrigation fluid can be adjusted by irrigation pump 110, which is configured as a variable speed pump. In some embodiments, the fluid flow rate of irrigation fluid is within a range of 60 to 120 mL/min inclusive. In one embodiment, the fluid flow rate of irrigation fluid is 80 mL/min.

Pressure measurements taken by at least one of pressure sensors 156 and 158 in the kidney are used as at least one of the feedbacks for controller 190 in controlling systems 100*a* and 100*b*. In accordance with at least one embodiment, controller 190 is configured to receive at least one pressure measurement value from pressure sensor 156 and/or 158, compare the measured pressure value to a predetermined pressure threshold, and based on the comparison, send a control command or otherwise control at least one of the bypass valve 132, the at least one valve (136 and/or 138), and the aspiration pump 115. As discussed further below, controller 190 also has the capability of receiving input from other sensors in system 100 (e.g., pressure sensor 150 in the irrigation channel 102, flow rate sensor 140 in the irrigation channel 102), flow rate sensor 144 in the aspiration channel 1043 and control other components of system 100 (e.g., irrigation pump 140, laser 107).

During the procedure, an initial target, pressure value (e.g., 40 $cmH_2O$, an example of a predetermined pressure threshold) in the kidney is used as a basis by the controller 190 (also referred to as a control system) for controlling the aspiration pump 115 and the flow of fluid in the aspiration channel 104 in an initial operating mode. The aspiration pump 115 is also configured as a variable speed pump and can be adjusted such that the pressure in the kidney is at the initial target pressure value. For example, if the initial pressure in the kidney is too low, the controller 190 can slow down aspiration pump 115 so that less fluid is removed from the kidney, and if the initial pressure in the kidney is too high, controller 190 can speed up the aspiration pump 115 to remove more fluid from the kidney. In accordance with some embodiments, the fluid flow rate in the aspiration channel 104 is within a range of 60 to 150 mL/min inclusive. The internal pressure of the kidney will change as the procedure progresses further, and this internal kidney pressure as measured by sensor(s) 156 and/or 158 is used by controller 190 in controlling other components in system 100.

Figure 2:
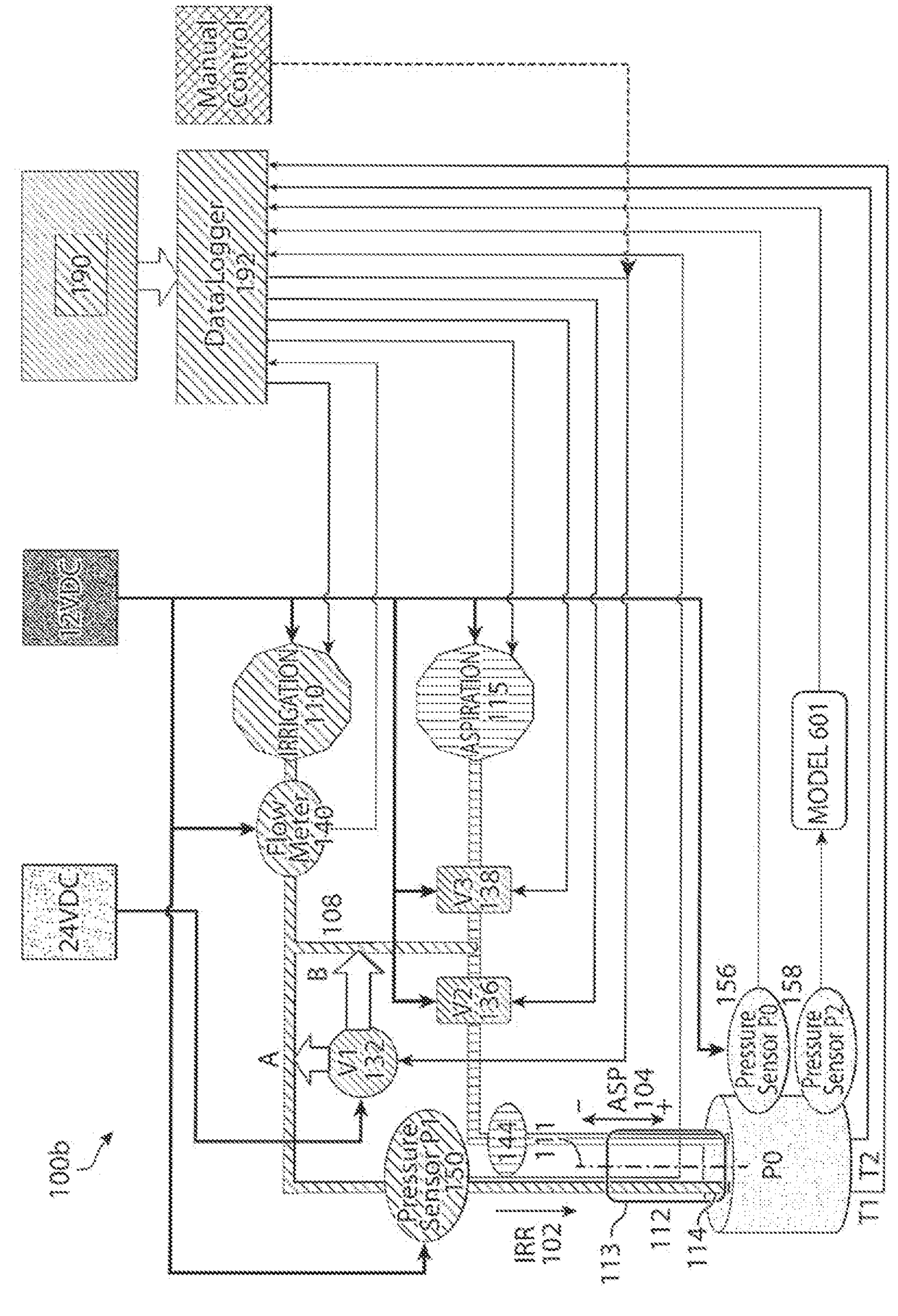
FIG. 2 is a block diagram of the irrigation and aspiration system of FIG. 1B.

FIG. 2 is a block diagram of the irrigation and aspiration system of FIG. 1B, and FIG. is a time graph showing aspects of the functionality of the system of FIG. 1B. However, it is to be appreciated that the functionality shown in FIG. 5 also applies to system 100*a* of FIG. 1A.

Figure 5:
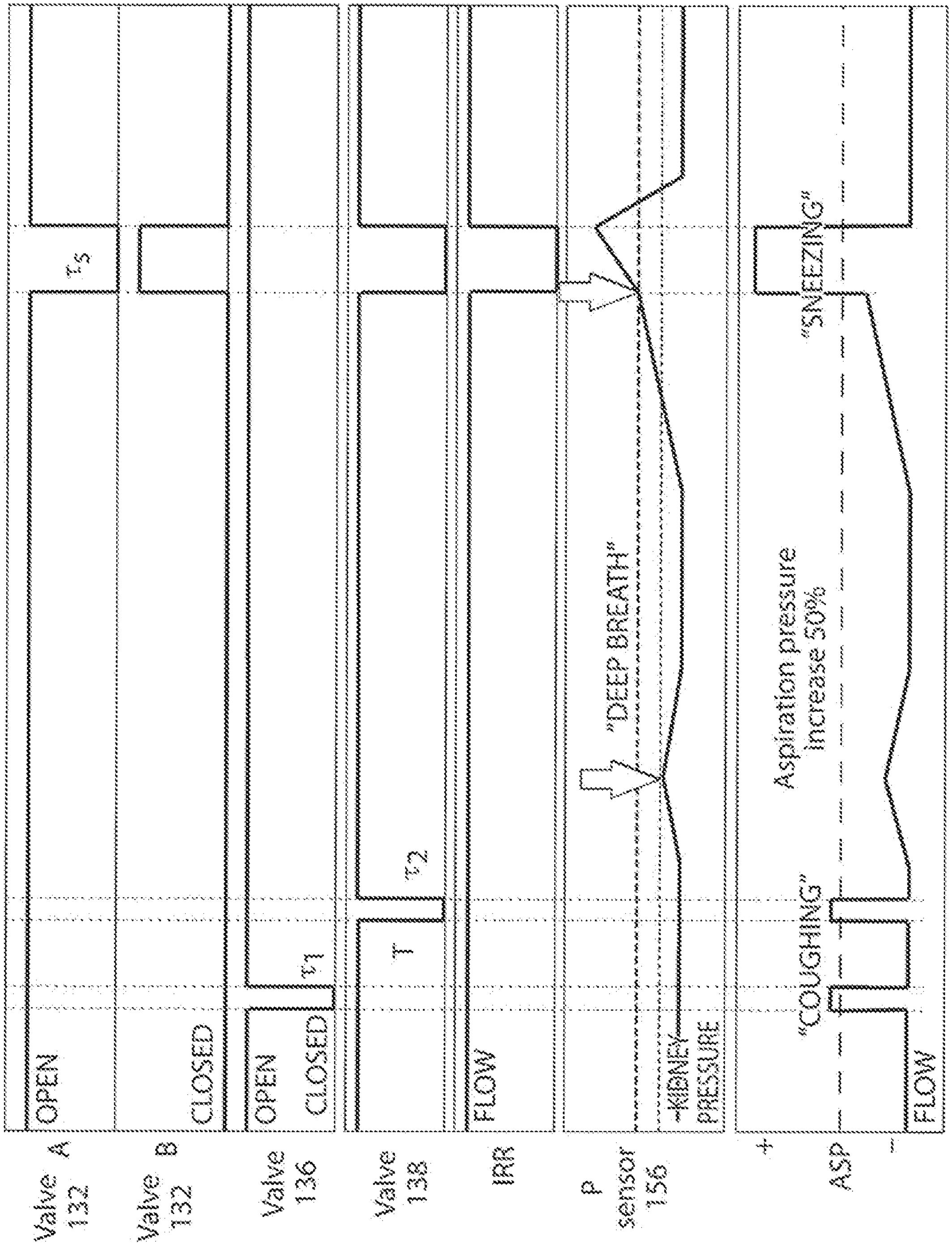
FIG. 5 is a time graph showing aspects of the functionality of the system of FIG. 1B.

During a normal operation mode, as shown on the left side of the graph in FIG. 5, channel "A" of bypass valve 132 is open and channel "B" (i.e., bypass channel 108) of bypass valve 132 is closed. According to one embodiment, bypass valve 132 is configured as a three-way solenoid pinch valve. Irrigation fluid is pumped by irrigation pump 110 through irrigation channel 102 through channel A of bypass valve 132 and along the irrigation channel until it exits the distal end of the irrigation channel 102 into the kidney. As noted previously, the aspiration channel 104 is configured to provide pulsed fluid flow via the at least one valve 136 and/or 138, which in FIG. 5 includes both valves 136 and 138, but it is to be appreciated that the pulsed fluid flow may be implemented with one valve, as shown in FIG. 1*a*. The left side on the bottom of FIG. 5 shows the cumulative effect of the pulsed aspiration flow, which resembles a "coughing" regime, where short pulses of back pressure are created along the fluid within the aspiration channel 104. As the laser tires and ablates kidney stone material, ablation product particles are generated in the vicinity of the distal end of the aspiration channel 104. As mentioned previously, the pulsed flow in the aspiration channel 104 facilitates mixing of these particles and reduces the risk of clogging in the aspiration channel 104.

Controller 190 can be used to monitor and control the liquid pressure in the kidney. The controller 190 receives pressure measurements from pressure sensor(s) 156 and/or 158 and analyzes this data. In some embodiments, controller 190 compares die measured pressure value to a predetermined pressure threshold, and based on the comparison, sends a control command to at least one of bypass valve 132, at least one valve 136, 138, and aspiration pump 115.

According to at least one embodiment, the controller 190 is configured to calculate a measured pressure value per unit of time and determine whether the measured pressure value per unit of time meets or exceeds one or more threshold values. In response, the controller 190 sends a control command to one or more components in system 100Q, such as bypass valve 132, at least one valve 136, 138, and/or aspiration pump 115. In accordance with additional aspects, controller 190 may also receive input from other sensors, such as pressure sensor 150 in the irrigation channel and/or fluid flow rate sensor 140 in the irrigation channel, and/or fluid flow rate sensor 144 in the aspiration channel, and send control commands to components in system 100, such as laser source 107.

In accordance with certain embodiments, an initial or primary clog detection operating mode of system 100 can be implemented by the controller 190. A clog in the aspiration channel 104 will cause an increase m pressure in the kidney since fluid is not being effectively removed from the kidney and irrigation fluid from irrigation channel 102 is still entering the kidney. According to one embodiment, the initial or primary clog detection operating mode may commence when controller 190 calculates a measured pressure value per unit of time and determines that the measured pressure value per unit of time meets or exceeds a first predetermined threshold value, in response, controller 190 sends a control command to the aspiration pump 115 such that a flow rate of fluid in the aspiration channel 104 is increased. According to one method, the controller 190 determines whether the measured pressure value is less than a first pressure threshold and increases a rate of the pulsed fluid flow when the measured pressure value meets or exceeds the first pressure threshold. For example, when the measured pressure value from pressure sensor(s) 156 and/or 158 is a predetermined percentage or range of percentages (e.g., 25%) over a target value (e.g., 40 $cmH_2O$) for a predetermined time period (e.g., 2 s), the fluid flow rate in aspiration channel 104 can be increased by the aspiration pump 115 via controller 190. For example, the measured pressure value may be within a range of 5 to 100% (inclusive) over the target value for a time period within a range of 0.2 to 10 s (inclusive) for the primary clog detection operating mode to be implemented. In another example, the measured pressure value may be within a range of 20 to 30% (inclusive) over the target value for a time period within a range of 1 to 5 s (inclusive) for the primary clog detection operating mode to be implemented. According to some embodiments, pressure monitoring is performed continuously. In some embodiments, the aspiration fluid flow rate can be increased from 100 mL/min up to a maximum of 150 mL/min. In accordance with certain embodiments, the aspiration fluid flow rate is increased such that the negative pressure in the aspiration channel is increased by 50%. In some embodiments, the aspiration fluid flow rate is increased such that the negative pressure in the aspiration channel is increased within a range of 5 to 100% inclusive. In certain embodiments, the aspiration fluid flow rate is increased such that the negative pressure in the aspiration channel is increased within a range of 25 to 75% inclusive. According to one embodiments, the measured pressure value that is used as a basis for the first predetermined threshold value or first pressure threshold is 50 $cmH_2O$ (25% over a target of 40 $cmH_2O$). A target pressure value of 40 $cmH_2O$ is used herein as an example, but it is to be appreciated that other target pressure values are also within the scope of this disclosure.

An example of the primary clog detection mode is shown in the intermediary region of FIG. 5, which resembles a "deep breath" regime, where the negative pressure in the aspiration channel 104 is increased over a period of time, e.g., the time period between the two arrows in FIG. 5. This additional "sticking in" action of the aspiration channel 104 resembles a human taking a deep breath.

In accordance with certain embodiments, a secondary clog detection operating mode of system 100 can also be implemented by controller 190. In this instance, controller 190 is configured to determine whether the measured pressure value per unit of time meets or exceeds a second predetermined threshold value. This mode may be triggered when the response during the primary clog detection operating mode (i.e., increasing the fluid flow rate in the aspiration channel) fails to decrease the kidney pressure down to an acceptable level. In at least one embodiment, if the pressure in the kidney drops to an acceptable level (e.g., 40 $cmH_2O$) within a predetermined time period (e.g., 5 seconds), then the controller 190 can decrease the speed of the aspiration pump 115 back down to the initial level. According to some embodiments, this predetermined time period is within a range of 2 to 30 seconds inclusive. However, if the pressure fails to drop within the predetermined time period, then the controller 190 can implement a secondary clog detection operating mode, as described below.

According to one embodiment, in response to the controller 190 determining that the measured pressure value per unit of time meets or exceeds a second predetermined threshold value, controller 190 sends a control command to the bypass valve 132 such that the bypass channel 108 is opened and the irrigation channel 102 is fluidly coupled to the aspiration channel 104 and irrigation fluid is directed toward the distal end of the aspiration channel 104. According to one method, the controller 190 determines whether the measured pressure value is less than a second pressure threshold, and directs fluid flow from the irrigation channel 102 into the aspiration channel 104 when the measured pressure value meets or exceeds the second pressure threshold. In addition, the controller 190 may send a control command to the valve 138 such that valve 138 is closed to stop a flow of fluid from the distal end toward the proximal end of the aspiration channel 104. This allows the irrigation fluid to flow to the distal end of the aspiration channel 104 without any counteracting force pumping it in the other direction via the aspiration pump 1S. In some embodiments, controller 190 may send a control command to the aspiration pump 115 to halt pumping (e.g., power off). According to one example, when the measured pressure value is a predetermined percentage or range of percentages (e.g., 50%) over a target value (e.g., 40 $cmH_2O$) for a predetermined time period (e.g., 2 seconds), fluid flow from the irrigation channel 102 may be directed into the aspiration channel via controller 190 (via bypass valve 132). For example, the measured pressure value may be within a range of 5 to 100% (inclusive) over the target value for a time period within a range of 0.2 to 10 s (inclusive) for the secondary clog detection operating mode to be implemented. In another example, the measured pressure value may be within a range of 30 to 70% (inclusive) over the target value for a time period within a range of 1 to 5 s (inclusive) for the secondary clog detection operating mode to be implemented. According to one embodiment, the measured pressure value that is used as a basis for the second predetermined threshold value is 60 $cmH_2O$ (50% over a target of 40 $cmH_2O$).

The secondary clog detection operating mode is shown on the right side of the graph in FIG. 5. During this secondary clog detection operating mode, valve 138 may be closed, and with irrigation fluid being bypassed into the aspiration channel 108, the pulsed flow of fluid in the aspiration channel 104 is interrupted. In addition, during this mode the controller 190 closes channel A of bypass valve 132 so that irrigation fluid is not directed to the distal end of the irrigation channel 102 (i.e., irrigation fluid flow is shut off or terminated) which would further increase the pressure in the kidney. Valve 138 and channel A of bypass valve 132 are closed for a predetermined time period n (also referred to herein as the switching time period or bypass time duration). In addition, the bypass channel 108 (channel B of bypass valve 132) is open for the predetermined time period $\tau_s$. In some embodiments, predetermined time period $\tau_s$ is within a range of 0.5 to 3.0 s inclusive. In other embodiments, predetermined time period $\tau_s$ is one second. In some embodiments, r, is based on a predetermined fluid volume, such as 2 milliliters (ml). According to certain embodiments, the predetermined fluid volume may be within a range of 0.5 to 10 ml inclusive. In accordance with other embodiments, backpressure pulses may be implemented in the aspiration channel 104 (via valves 136 and 138) based on the measured pressure values. For instance, in response to a measured pressure value or a rate/change of measured pressure, backpressure pulses may be implemented in the aspiration channel 104 using valve 136 and/or 138. These backpressure pulses may function to dislodge a clog in the aspiration channel 104.

The right side on the bottom of FIG. 5 shows the effect of the interrupted and redirected irrigation fluid flow, which resembles a "sneezing" regime, where fluid pressure in the aspiration channel 104 is increased for a longer period of time than in the "coughing regime." in much the same way that human "sneeze" is typically longer (and of a greater force) than a human "cough." Once predetermined time period r, has terminated, then channel A of bypass valve 132 is opened and bypass channel 108 (channel B) of bypass valve 132 is closed. In some embodiments, valve 138 is also opened. This configuration is indicated on the far right of FIG. 5 (which indicates that irrigation fluid flow is restored to the irrigation channel 102) and pulsed aspiration flow may also be restored if the measured kidney pressure is at an acceptable level. As shown in FIG. 5, the pressure level in the kidney drops after the secondary clog detection operating mode has been implemented. However, if the pressure level in the kidney fails to decrease to an acceptable level after implementing the secondary clog detection operating mode, then this mode may be repeated a number of times until the kidney pressure falls to an acceptable level. The number of repetitions may be limited so as to not cause harm to the kidney. In some instances, the secondary clog detection operation mode (i.e., implementation of the bypass channel 108 for a predetermined time period) may be repeated up to 5 consecutive times.

The control scheme exemplified in FIG. 5 is characterized in certain aspects by the avoidance or prevention of sudden or acute increases and decreases in kidney pressure. The kidney is capable of withstanding an increase in pressure over a longer period of time to a predetermined maximum value (e.g., 250 $cmH_2O$), but if this threshold value is reached in a shorter or rapid amount of time (e.g., less than 30 s), the kidney may be harmed. The control scheme outlined in FIG. 5 is intended to capture this ability of the kidney by avoiding sudden increases (and decreases) in pressure. In accordance with certain embodiments, the disclosed control schemes prevent the kidney from reaching 250 $cmH_2O$ (from 40 $cmH_2O$) in less than 30 s, which would be harmful to the kidney.

Figure 6:
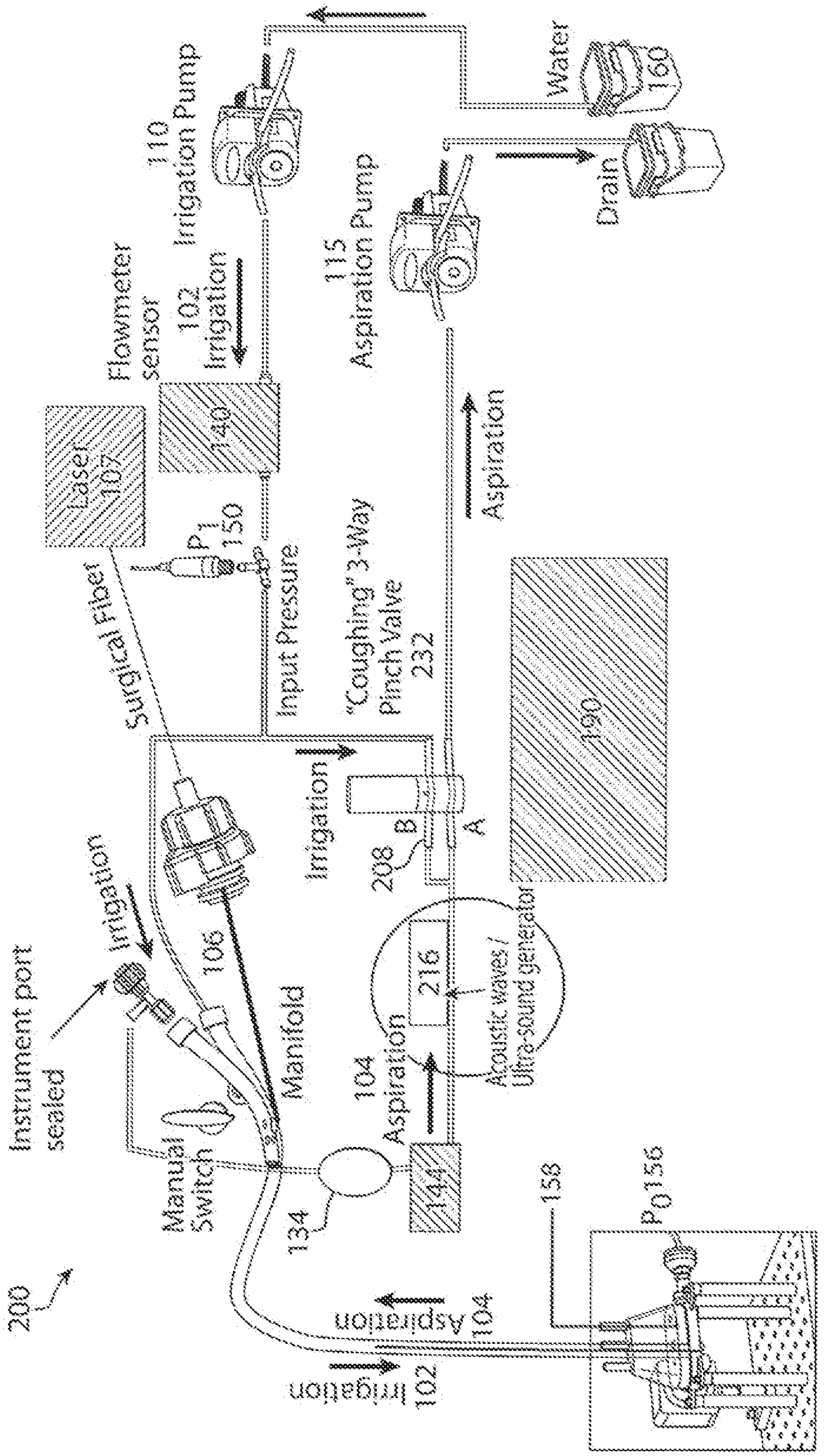
FIG. 6 is a schematic representation of yet another example of an irrigation and aspiration system in accordance with aspects of the invention.

Another non-limiting example of an irrigation and aspiration system in accordance with one embodiment is indicated generally at 200 in FIG. 6. System 200 has many of the same components as systems 100*a* of FIGS. 1A and 100*b* of FIG. 1B, but in this configuration, valves 136 and 138 are replaced by an ultrasonic transducer 216, and bypass valve 232 in combination with bypass channel 208 is configured slightly differently. Bypass channel 208 is still configured to fluidly couple the irrigation channel 102 with the aspiration channel 104, but in this instance, channel "A" of first valve 232 is in fluid communication with the aspiration channel 104 instead of the irrigation channel 102. During a normal mode of operation, channel A is open and channel B is closed so that fluid flows from the distal end to the proximal end of the aspiration channel 104. Ultrasonic transducer 216 is configured to mechanically vibrate the aspiration channel 104. The vibrations can be configured (i.e., through controller 190) to create back pressure in the aspiration channel in a similar manner as pinch valve(s) 138 and 136 of systems 100*a* and 100*b*. As indicated in FIG. 6, according to one embodiment ultrasonic transducer 216 is disposed between the distal end of aspiration channel 104 and the bypass channel 208.

FIG. 3 is a perspective view of the distal end of one example of a ureteroscope 105 in accordance with at least one embodiment. The laser source 107 is configured to emit laser radiation, and an optical fiber 106 is coupled to the laser source 107 and is configured to transmit the laser radiation within close proximity to the distal end of the aspiration channel 104, which is indicated in FIG. 3. The optical fiber 106 extends from the proximal end 113 to the distal end 114 of the catheter shaft 112 (e.g., see FIG. 21. In certain embodiments, system 100 may comprise one or more components of an imaging system. For example, ureteroscope 105 may comprise a camera 165, as shown in FIG. 3 that is disposed at the distal end of the catheter shaft 112. In addition, at least one outlet 146 is defined at the distal end of the irrigation channel 104, in one embodiment, the at least one outlet 146 is configured to direct irrigation flow at an angle relative to a central axis 111 (e.g., see FIG. 2) of the catheter shaft 112 that is within a range of 0 degrees to 170 degrees inclusive. In some embodiments, the flow angle is within a range of 10 to 90 degrees inclusive.

Besides a camera 165, in some embodiments ultrasound may be used for purposes of providing visualization of the treatment area in the kidney. For example, ultrasound can be applied to the skin of the patient in the vicinity of the kidney and the resulting imagery can be displayed on a screen for the doctor to use. In some instances, ultrasonic images can be used as a source of control. For example, a baseline image can be taken prior to the procedure, and used as a source of comparison throughout the procedure in controlling the pressure within the kidney.

According to one or more embodiments, systems 100*a* and 100*b* may comprise one or more temperature sensors. Temperature sensors 170*a* and 170*b* are shown in systems 100*a* and 100*b* of FIGS. 1A and 1B respectively. In some embodiments, at least one of temperature sensors 170*a* and 170*b* are positioned within an interior of the kidney, i.e., in the vicinity of the treatment area, external to the ureteroscope, as is the same with pressure sensor 156. In other embodiments, the catheter shaft may be configured with one or more temperature sensors. e.g., at the distal end of the catheter shaft. According to at least one aspect, temperature measurements are taken by the temperature sensor and used by the controller 190 to ensure that the temperature does not get too high, which would harm the kidney. As will be appreciated, heat generated by the laser can increase the fluid temperature within the kidney. In some instances, the controller 190 can control one or more components of system 100, e.g., the speed of the aspiration pump 115 and/or the irrigation pump 110, and/or the laser source 107 to ensure the temperature within the kidney is maintained within an acceptable range, e.g., within a range of 20 to 45° C. inclusive.

In accordance with another aspect, systems 100*a* and 100*b* may also be configured such that one or more components can be operated or otherwise controlled manually. For example, as shown in FIG. 2, bypass valve 132 may be operated manually by an operator of the system (e.g., a doctor). Manual pump 134 (e.g., see FIGS. 1A and 1B) disposed on the aspiration channel 104 can be used by a user to pump fluid through the aspiration channel 104.

Increasing Ablation Rates

In accordance with at least one aspect, during a lithotripsy procedure the ureteroscope 105 is manipulated to come in close proximity to the stone target, and the aspiration/irrigation system 100 is configured to detect that a stone is within the vicinity of the laser 106. This ability is based on the premise that the pressure and flow rate in the aspiration channel 104 will change (increase and decrease, respectively) when the entrance to the channel is partially blocked by a stone.

As indicated in FIG. 3, the optical fiber 106, which directs the light energy, is placed within, next to, or otherwise in close proximity to the aspiration channel 104. Functionally, this means that the distal end 103 of the optical fiber 106 is placed at the mouth (distal end) of the aspiration channel 104. In some embodiments, the optical fiber 106 may have its own channel, in other embodiments the optical fiber 106 may have its own lumen in the aspiration channel 104, and in still other embodiments the optical fiber 106 may be placed in the aspiration channel 104 and run the length of the aspiration channel 104. When the stone obstructs the aspiration channel 104 of the ureteroscope 105, the flow through the aspiration channel 104 will decrease while vacuum pressure increases. In accordance with one embodiment, a fluid flow rate sensor, such as fluid flow rate sensor 144 as shown in FIGS. 1A, 13, and 2 may be used to monitor the fluid flow rate in the aspiration channel 104. In some embodiments, the flow rate sensor 144 is attached or otherwise disposed at the distal end of the aspiration channel 104. Stone detection can be determined by the controller 190 detecting a decrease in fluid flow rate based on measured fluid flow rate values in the aspiration channel 104 and an increase of pressure in the kidney, which may be determined based on measured pressure values front at least one of pressure sensor 156 and pressure sensor 158. The controller 190 receives pressure and flow rate measurements from sensor 144 and at least one of sensor 156 and 158 and analyzes this data to determine whether a change in pressure and flow rate per unit of time meets or exceeds a predetermined limit or target value. For instance, according to one example, a 30% decrease (change) in flow rate and a 25% increase (change) in pressure would indicate the presence of a stone. According to some embodiments, the time duration associated with stone detection is within a range of 1 to 10 seconds inclusive.

Using the controller 190, laser operation can be synchronized to the detection of the stone, and fire once the stone is in close proximity to the optical fiber. This has been shown to substantially increase ablation rates. Once the stone is determined to be within the vicinity of the laser, the vacuum generated in the aspiration channel 104 (i.e., vacuum pressure) is used to hold the stone close to the optical fiber 106 at the distal end of the aspiration channel 104. In some instances, the presence of the stone itself produces enough vacuum pressure to hold it in place, but according to at least one embodiment, the vacuum pressure in the aspiration channel 104 may be further increased (e.g., via aspiration pump 115) to ensure that the stone is firmly held in position. This vacuum increases the ablation rate by increasing the 1) contact time between the fiber and the stone. Besides increasing the ablation rate, an additional benefit is that laser discharge only occurs when the stone is within the target area, which limits the potential for collateral damage. The vacuum attachment along with laser synchronization therefore increase ablation rates and minimize unwanted laser discharge.

In accordance with another aspect, the laser is configured to emit pulsed laser radiation, which can be synchronized with pulsing of fluid flow through the aspiration 104 channel. For example, once a stone is in the optimal targeting position (i.e., the mouth or distal end of the aspiration channel 104) a pre-determined laser pulse sequence (e.g., between 1-1000 laser pulses) are directed at the stone, which is followed by pulsing the pressure within the aspiration channel 104 until the stone is in the optimal target position once again. This cycle is then repeated. The efficiency of stone ablation is also increased with this technique. In some embodiments the pulsing of the fluid flow and laser pulses is not, synchronized. According to one non-limiting example of such an embodiment, the frequency of the pressure pulsing may have a minimum of 0.1 Hz and the repetition rate of the laser pulses can be in a range of about 3 Hz-3000 Hz.

In accordance with another aspect, the aspiration channel 104 may contain a temperature sensor (not explicitly shown in the figures) to measure the temperature of the fluid flowing in the aspiration channel 104. This feature can aid in ensuring that tissue does not overheat. For instance, detecting an increase in temperature (above a predetermined target) of the return fluid in the aspiration channel 104 may create the need (implemented by commands from the controller 190) to increase the speed of fluid exchange at the treatment site or to decrease the power of the laser radiation emitted by the laser source. Besides preventing tissue damage from overheating, this feedback mechanism also keeps laser power at a safe level for ensuring a high ablation rate.

Maintaining Equilibrium—Calculations

To define parameters of the fluidic pump system more precisely, and maintain equilibrium of fluid flow and pressure, certain calculations can be done and are outlined below.

First, using some modeling techniques, one or more parameters of the components of the system can be defined, such as the pumps. Per the Hagen-Poiseuille equation, the pressure for an increase in the flow rate can be calculated. The Hagen-Poiseuille equation defines the pressure differential δP (Pascal), which is needed to produce a volumetric flow rate Q ($m^3$/sec) of a fluid which has a viscosity μ (Pa-sec) in a channel with inner radius r (m) and length L(m).

The pressure differential: $\delta P=8\ \mu LQ/\pi r^A$

μ=dynamic viscosity. For 0.9% saline: $\mu=1.02*10^{-3}$) Pa-sec

L=the length of the scope. 1=0.7 m

Q=the volumetric flow rate. Q:=70 mL/min=1.17 mL/sec=$1.17*10^{-6}$ $m^3$/Sec r=the radius of the aspiration channel, r=0.6 mm=$6*10^{-4}$ $m^3$/sec The pressure differential for aspiration can thus be calculated. According to one example, the average flow rate through the ureter/bladder-urethra and around the outer body of the scope is about 30 mL/min, and a maximum value is 100 mL/min. This leaves about 70 mL/min to go through the aspiration channel.

$$\delta P_{asp} = 8*1.02*10^{-3}*0.7*1.17*10^{-6}/\pi*1296*10^{-16} == 1.63*10^4 \text{ Pa} = 16300 \text{ Pa} = 164 \text{ CM of Water} = 2.36 \text{ psi}$$

The result of 2.36 psi is the pressure which needs to be applied on the proximal end of the scope to "suck" the fluid out of the kidney. This is a negative pressure. Assuming that the working barometric pressure in the kidney may be 40 CM (where CM=centimeter water column ($cmH_2O$)), the negative pressure on the proximal end of the scope will be:

$$\text{Aspiration pressure } Pasp = 40 \text{ CM} - 164 \text{ CM} = -124 \text{ CM} = -1.8 \text{ psi}$$

This result implies that by applying −1.8 psi, a flow rate of 100 mL/min can be created. In addition, if a positive pressure were to exist in the kidney, this flow rate would reduce this positive pressure in the kidney.

Similarly, the irrigation pressure can be calculated. In one example, the irrigation flow rate is 100 mL/min. which is $1.67*10^{-6}$ $m^3$/sec; the length of the scope is 0.7 n and the radius of the irrigation channel is also 0.6 mm.

$$\delta P_{irr} = 8*1.02*10^{-3}*0.7*1.67*10^{-6}/\pi*1296*10^{-16} == 2.32*10^4 \text{ Pa} = 23200 \text{ Pa} = 233 \text{ CM} = 3.36 \text{ psi}$$

The result of 3.36 psi is the pressure differential that is needed to have a flow rate of 100 mL/min through a channel having a 1.2 mm diameter and a length of 0.7 m. Assuming that there is still a need for about 40 CM of water pressure inside the kidney, the irrigation pump must deliver about 273 CM or about 4 psi of pressure.

The analysis presented above indicates that the irrigation pump should be configured to produce at least 4 psi of pressure and a flow rate of at least 100 mL/min, and the aspiration pump should be configured to produce at least 1.8 psi of negative pressure and a flow rate of at least 70 mL/min.

Control

The controller 190 can utilize a control program to control operation of system 100. In general terms, the controller 190 includes a data acquisition component 192 (e.g., data logger of FIG. 2), a storage component (not shown) and a viewing component (not shown).

The data acquisition component 192 queries and acquires measurement data from one or more of the sensors, e.g., pressure and/or flow sensors, which is then processed by the controller 190. The controller 190 can also receive input from a user, which can be used by the control program. The information can then be processed and used by the controller 190 to control the laser source 107, valves 132, 136, 138, irrigation pump 110, and/or aspiration pump 115. The diagram of FIG. 2 indicates that control of these components goes through the data acquisition component 192, but it is to be appreciated that the controller 190 can directly control these components. For instance, valve action is controlled through a voltage signal sent by the controller 190.

As mentioned above, the controller 190 can be programmed with a control program that utilizes pre-set or predetermined target values (that can be stored) or manually controlled values for one or more of the laser source 107, valves 132, 136, 138, and pumps 110, 115 (as well as ultrasonic transducer 216) based on measurements received from the data acquisition component 192 and sent by one or more sensors of systems 100*a*, 100*b* (or system 200). It is to be appreciated that the controller 190 can also control the data acquisition component 192 to initiate data acquisition actions, i.e., measurement data or other signal data. According to at least one embodiment, one or more of the pressure and/or flow sensors can obtain measurement data at various time intervals or in a continuous manner.

The control program used by the controller 190 can be configured to perform a number of different control actions or control states to achieve one or more desired results, be it synchronizing laser firing with stone attachment, ensuring that stone/fiber contact is persistent, clearing the aspiration channel of clogs, or maintaining equilibrium within the kidney and system. For instance, pressure and flow abnormalities can be adjusted for by opening or closing channel valves and adjusting fluid pump speed.

As previously mentioned, one or more (pressure, fluid flow) sensors can be used to assist with maintaining a target equilibrium pressure in the kidney. In addition, sensor(s) in the irrigation channel 102 (e.g., pressure sensor 150 and/or flow rate sensor 140) can also be used to ensure that the irrigation channel 102 is properly functioning, and can also be used to detect potential damage. For example, if the irrigation pump 110 is pumping (i.e., turned on) but the sensor(s) fail to detect any fluid flow in the irrigation channel 102, then this indicates a system error. Further, if the pressure sensor(s) measure values that are too high or too low, then this also indicates a system error.

Example

Functions and advantages of the embodiments of the systems and techniques disclosed herein may be more fully understood based on the example described below. The following example is intended to illustrate various aspects of the disclosed aspiration and irrigation system but is not intended to fully exemplify the full scope thereof.

Example—Laser Power and Aspiration Fluid Flow Rate Experiment

Experiments were performed to test the capability of utilizing fluid flow in the aspiration channel of the ureteroscope to achieve higher laser powers. The higher laser powers can provide several benefits, including increased ablation rates, which can potentially shorten the procedure time. Fluid flow in the aspiration channel can be used to control temperatures within the vicinity of the laser, which allows tissue to be maintained within a safe temperature range.

Figure 7:
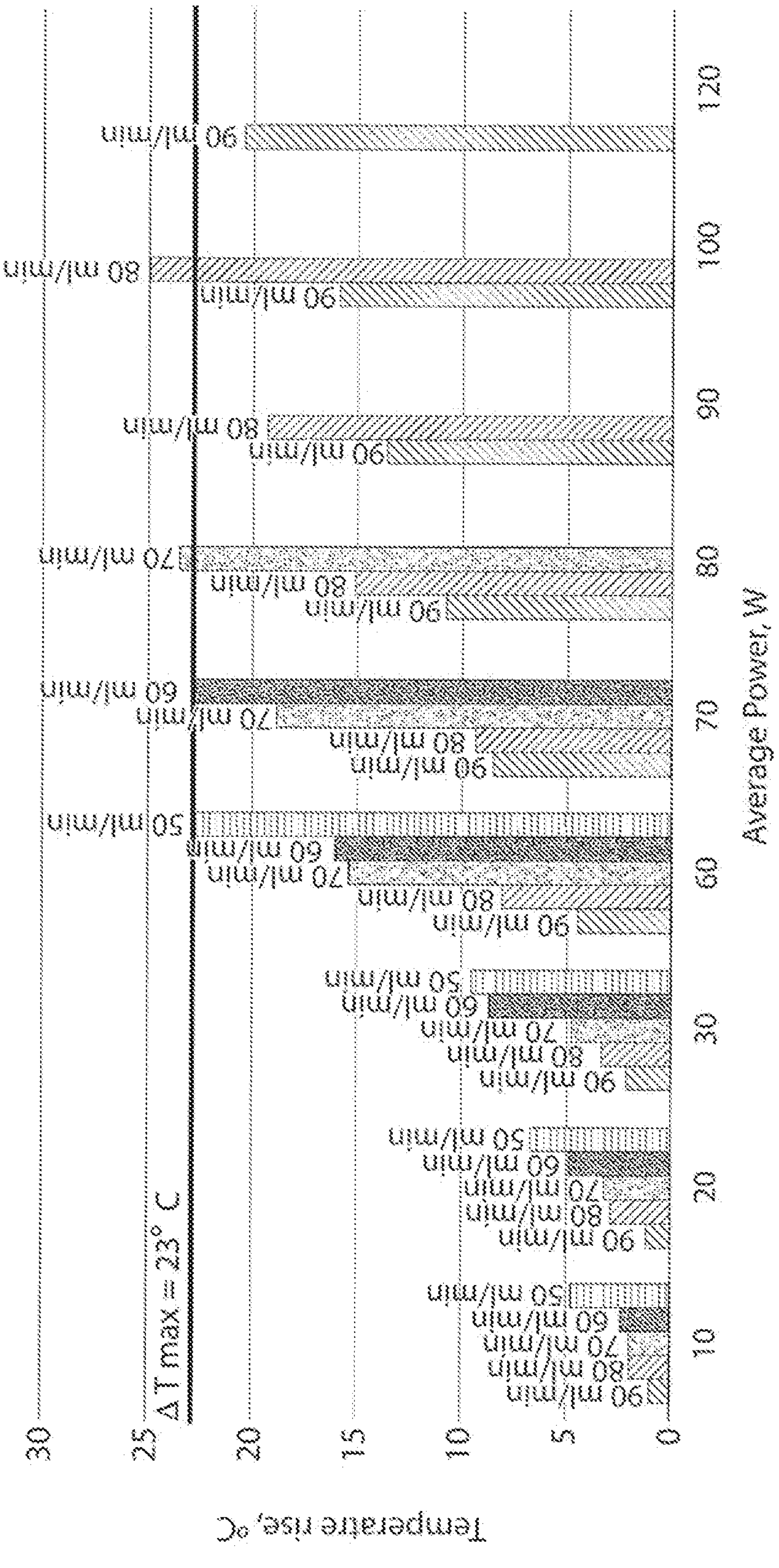
FIG. 7 is a graph showing the results from an experiment in accordance with aspects of the invention.

The experiments were conducted using a silicone model of a urinary tract filled with saline solution that served for insertion of the shaft of a ureteroscope fitted with a Thulium fiber laser and actuated irrigation and aspiration flows using tubing. The laser was operated at 1 Joule (J) pulse energy, 500 Watt (W) peak power and a variable pulse repetition rate for nine different average powers (10, 20, 30, 60, 70, 80, 90, 100, and 120 W). The aspiration flow rate was tested at values from 50 mil/min to 90 ml/min (as shown in FIG. 7), and the irrigation flow was set at about a 10 ml/min higher rate than the aspiration flow. Two temperature sensors (Thermocouple type K) were placed at about 20-30 mm above and below the distal end of the shaft, which had a 3 mm outer diameter.

Temperature measurements were obtained after reaching saturation and temperature stable levels, which took up to 15 minutes. A maximum temperature increase (delta) was selected as 23° C. with an initial fluid temperature of 20° C. and a maximum allowed temperature of 45° C. The results are shown in FIG. 7, and indicate that increasing the aspiration fluid flow rate from 50 to 90 ml/min allows for the safe use of 2× more laser power—from 60 W to 120 W. In contrast, at a conventional flow rate of 10 ml/min with natural aspiration through the access sheath, the maximum laser power that can be safely used is typically 20-25 W.

The aspects disclosed herein in accordance with the present invention, are not limited in their application to the details of construction and the arrangement of components set forth in the following description or illustrated in the accompanying drawings. These aspects are capable of assuming other embodiments and of being practiced or ofbeing carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising." "having." "containing;" "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the present invention.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. An irrigation and aspiration system, comprising:

a catheter shaft having a proximal end and a distal end, the distal end configured to be in fluid communication with an interior of a kidney;

an irrigation channel extending through the shaft from the proximal end to the distal end;

an aspiration channel extending through the shaft from the proximal end to the distal end;

a bypass channel fluidly coupled with the irrigation channel and with the aspiration channel;

a bypass valve configured to control a level of fluid communication between the irrigation channel and the aspiration channel via the bypass channel;

an aspiration pump in fluid communication with the aspiration channel and configured to pump fluid from a distal end toward a proximal end of the aspiration channel;

at least one valve disposed on the aspiration channel and configured to provide a pulsed flow of fluid in the aspiration channel;

a pressure sensor configured to be in fluid communication with an interior of the kidney; and a controller in communication with the pressure sensor, the bypass valve, the at least one valve, and the aspiration pump, the controller configured to:

receive at least one pressure measurement value from the pressure sensor, compare the measured pressure value to a predetermined pressure threshold, and based on the comparison, send a control command to at least one of the bypass valve, the at least one valve, and the aspiration pump;

wherein the at least one valve includes a first valve disposed on the aspiration channel between the bypass channel and the aspiration pump and a second valve, the second valve disposed on the aspiration channel between the bypass channel and the distal end of the aspiration channel; and wherein the controller is configured to implement the pulsed flow of the fluid by sending a control command to close the first valve for a predetermined time duration $\tau 1$ and close the second valve for a predetermined time duration $\tau 2$ in repetitive cycles, where $\tau 1$ and $\tau 2$ are separated by a predetermined time period t and each cycle is of a time period T.

2. The system of claim 1, wherein the controller is configured to calculate a measured pressure value per unit of time and determine whether the measured pressure value per unit of time meets or exceeds a first predetermined threshold value, and in response send a control command to the aspiration pump such that a flow rate of fluid in the aspiration channel is increased.

3. The system of claim 2, wherein the measured pressure value used as a basis for the first predetermined threshold value is 50 $cmH_2O$.

4. The system of claim 2, wherein the controller is configured to determine whether the measured pressure value per unit of time meets or exceeds a second predetermined threshold value, and in response send a control command to the bypass valve such that the bypass channel is opened and the irrigation channel is fluidly coupled to the aspiration channel and irrigation fluid is directed toward the distal end of the aspiration channel.

5. The system of claim 4, wherein the measured pressure value used as a basis for the second predetermined threshold value is 60 $cmH_2O$.

6. The system of claim 1, wherein the bypass valve is configured as a three-way solenoid pinch valve and at least one of the at least one valves is configured as a two-way solenoid pinch valve.

7. The system of claim 1, wherein the pressure sensor is in proximity to an external surface of the catheter shaft.

8. The system of claim 1, further comprising a laser source configured to emit laser radiation, and an optical fiber coupled to the laser source and configured to transmit the laser radiation within close proximity to the distal end of the aspiration channel, the optical fiber extending from the proximal end to the distal end of the catheter shaft.

9. A method of operating an aspiration and irrigation system, comprising:

providing a catheter shaft having a proximal end and a distal end, the distal end being in fluid communication with an interior of a kidney;

an irrigation channel extending through the shaft from the proximal end to the distal end;

an aspiration channel extending through the shaft from the proximal end to the distal end;

a bypass channel fluidly coupled with the irrigation channel and with the aspiration channel;

a bypass valve configured to control a level of fluid communication between the irrigation channel and the aspiration channel via the bypass channel;

an aspiration pump in fluid communication with the aspiration channel and configured to pump fluid from a distal end toward a proximal end of the aspiration channel;

at least one valve disposed on the aspiration channel and configured to provide a pulsed flow of fluid in the aspiration channel;

a pressure sensor in fluid communication with an interior of the kidney; and a controller in communication with the pressure sensor, the bypass valve, the at least one valve, and the aspiration pump;

providing pulsed fluid flow from a distal end to a proximal end of the aspiration channel, the distal end of the aspiration channel in fluid communication with an interior of a kidney;

measuring a pressure value in the interior of the kidney;

determining, with the controller, whether the measured pressure value is less than a first pressure threshold; and based on the comparison, send a control command to at least one of the bypass valve, the at least one valve, and the aspiration pump;

wherein the at least one valve includes a first valve disposed on the aspiration channel between the bypass channel and the aspiration pump and a second valve, the second valve disposed on the aspiration channel between the bypass channel and the distal end of the aspiration channel; and wherein the controller is configured to implement the pulsed flow of the fluid by sending a control command to close the first valve for a predetermined time duration $\tau 1$ and close the second valve for a predetermined time duration $\tau 2$ in repetitive cycles, where $\tau 1$ and $\tau 2$ are separated by a predetermined time period t and each cycle is of a time period T.

10. The method of claim 9, further comprising providing fluid flow from a proximal end to a distal end of an Irrigation channel, the distal end of the irrigation channel in fluid communication with the interior of the kidney;

determining whether the measured pressure value is less than a second pressure threshold, and directing fluid flow from the irrigation channel into the aspiration channel when the measured pressure value meets or exceeds the second pressure threshold.

11. The method of claim 10, wherein the fluid flow from the irrigation channel into the aspiration channel is directed through a bypass channel.

12. The method of claim 9, wherein $\tau 1$ and $\tau 2$ are within a range of 20 to 500 ms inclusive and the time period T is within the range of 0.5 to 3.0 s inclusive.

* * * * *